United States Patent [19]
Getman

[11] Patent Number: 4,764,594
[45] Date of Patent: Aug. 16, 1988

[54] RESIN SUPPORT FOR SOLID PHASE PEPTIDE SYNTHESIS

[75] Inventor: Daniel P. Getman, St. Louis, Mo.
[73] Assignee: Monsanto Company, St. Louis, Mo.
[21] Appl. No.: 31,823
[22] Filed: Mar. 30, 1987
[51] Int. Cl.[4] ..................... A61K 37/02; C08K 283/00
[52] U.S. Cl. ................................ 530/334; 525/54.11; 526/286; 526/347.1
[58] Field of Search ............................ 525/54.1, 54.11; 530/333, 334; 526/286, 346, 347.1

[56] References Cited

U.S. PATENT DOCUMENTS

| | | | |
|---|---|---|---|
| 3,995,094 | 11/1976 | Crosby et al. | 526/46 |
| 4,507,230 | 3/1985 | Tam et al. | 530/334 |
| 4,623,484 | 11/1986 | Carpino et al. | 530/334 |
| 4,680,339 | 7/1987 | Fong | 525/54.11 |

OTHER PUBLICATIONS

Samanen et al, "The p-methylsulfinylbenzyl Group, A Selectively Cleavable Carboxyl Protecting Group", 9th American Peptide Symposium in Toronto, pp. 225–228, 23–28 Jun. 1985.

Primary Examiner—Delbert R. Phillips
Assistant Examiner—Nathan M. Nutter
Attorney, Agent, or Firm—Linda L. Lewis; James W. Williams, Jr.

[57] ABSTRACT

A resin and method for preparing the resin for solid phase peptide synthesis. The resin has a sulfoxide linkage, which is stable to strong acid conditions. The sulfoxide linkage can be reduced to a sulfide linkage, which allows cleavage of the peptide from the resin under mild acid conditions.

4 Claims, No Drawings

RESIN SUPPORT FOR SOLID PHASE PEPTIDE SYNTHESIS

FIELD OF THE INVENTION

This invention relates to a resin support for solid phase peptide synthesis and a method of synthesizing the resin support.

SUMMARY OF RELATED ART

The synthesis of peptides is generally carried out through the condensation (or coupling) of the carboxyl group of an amino acid, and the amino group of another amino acid, to form a peptide bond. A sequence can be constructed by repeating the condensation of individual amino acids in stepwise elongation, or, in some cases, by condensation between two preformed peptide fragments (fragment condensation). In both types of condensations, the amino and carboxyl groups that are not to participate in the reaction must be blocked (or protected) with protecting groups. In addition, reactive side chain functionalities of the amino acids also need to be protected.

A successful synthesis of a large peptide by a series of condensation reactions must achieve nearly quantitative recoveries for each chemical step. This requirement has been met by solid-phase peptide synthesis, pioneered by R. B. Merrifield. In such a synthesis, the peptide chain is normally attached by a benzyl-type carboxyl-protecting group to an insoluble polystyrene resin. A first amino acid is attached to the resin through a benzylic ester linkage, is deprotected at its amino site, and coupled with a second amino acid carrying a protected α-amino group, to produce a protected dipeptide ester. The protecting group is removed with trifluoroacetic acid, neutralized to form the free amine with base, and coupled to a second N-protected amino acid. After many repetitions of these steps, the complete peptide is cleaved from the resin with acid treatment. By using the insoluble resin support it is possible to isolate the product of each coupling reaction by filtering the resin and washing it free of by-products and excess starting materials. Barany, G. and Merrifield, R. B., "The Peptides, Vol. 2", Academic Press, Inc., New York, 1979, pp. 1–284; and Kemp-Vellaccio, "Organic Chemistry", pp. 1030–1032 (1980).

In solid phase peptide synthesis, the peptide-resin link is critical to the synthesis procedure. The link must be stable to the deprotection of the amino blocking groups, which typically entails the use of concentrated acid. If the linkage is not stable to deprotecting conditions, the peptide will be prematurely cleaved from the resin. Additionally, the linkage must be readily cleaved upon completion of the synthesis of the peptide, preferably under conditions that will not damage the peptide being recovered.

A number of approaches have been taken to improve the peptide-resin linkage. Merrifield developed a phenylacetamidomethyl linkage which is more stable to the strong acid conditions required to deprotect the amino groups. (Stewart, J. M. and Young, J. D., *Solid Phase Peptide Synthesis*, second edition, Pierce Chemical Co., Rockford, Ill., pp. 11 and 12 and Gross, E. and Meienhofer, J., *The Peptides, Analysis, Synthesis, Biology*, Vol. 2, Academic Press, 1980, pp 3–250).

Because, as peptides become larger and more complex, they are less stable to the acidic condition necessary to deprotect and cleave, researchers developed a peptide resin link that can be cleaved by milder reagents. Wang developed a p-alkoxybenzyl alcohol resin that can be cleaved by 25% trifluoroacetic acid in dichloromethane. Stewart, Id. at 12, 13.

In an attempt to find milder conditions for cleavage, Tam, (U.S. Pat. No. 4,507,230) developed a method of reducing the acidity function of the strong acid used in cleavage, typically anhydrous hydrogen fluoride, by the use of a suitable weak base which would remain largely unprotonated and nucleophilic under the resulting acidic conditions.

None of the above references has disclosed a peptide-resin linkage for solid phase peptide synthesis which affords the combination of acid stability as well as ready cleavage under mild acid conditions.

J. M. Samanen and E. Bradelis disclose in their paper "The p-Methylsulfinylbenzyl Group, A Selectively Cleavable Carboxyl Protecting Group," 9th American Peptide Symposium in Toronto, June 23–28, 1985, a p-methylsulfinylbenzyl group which is useful as a carboxyl protecting group to be used in solution phase peptide synthesis. The sulfoxide substituted benzylic ester linkage is stable to the trifluoroacetic acid conditions used to deprotect the amino groups. When the sulfoxide is reduced to a sulfide, the ester group is "unlocked" and is cleavable in anhydrous trifluoroacetic acid. This protecting group has not been disclosed for use in solid phase peptide synthesis.

We have discovered a resin for solid phase peptide synthesis that provides both stability to strong acid conditions and ready cleavage under relatively mild conditions to provide a peptide and a method for synthesizing the resin.

SUMMARY OF THE INVENTION

The Resin

The present invention involves a resin for solid phase peptide synthesis and a method for synthesizing the resin. The resin comprises the structure

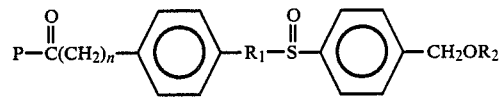

where $R_1$ is an alkyl having from 1 to 20 carbons, $R_2$ is hydrogen, acyl or carboxyl terminal N-blocked amino acid, P is the polymer support and n is from 0 to 20.

Synthesis I

A method of synthesizing a resin for solid phase peptide synthesis comprising (1) reacting an ester of the structure

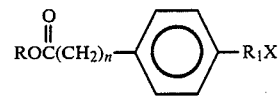

where X is a halogen, n is from 0 to 20, $R_1$ is an alkyl having from 1 to 20 carbons and R is an acid protecting group, with a mercaptobenzyl alcohol to form a sulfide of the structure,

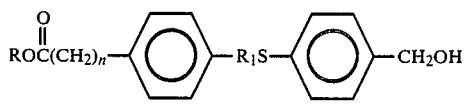

(2) oxidizing the sulfide to form a sulfoxide of the structure,

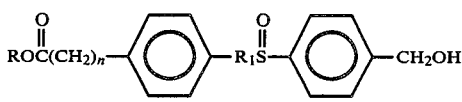

(3) esterifying the sulfoxide with a carboxyl terminal N-blocked amino acid, $R_2$, to form an ester of the structure,

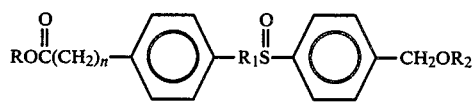

(4) removing the acid protecting group, R, from the ester to form an acid of the structure

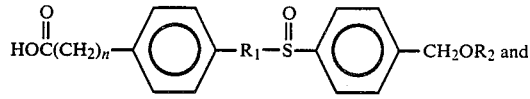

(5) anchoring the sulfoxide to a functionalized polymer, P, to form said resin of the structure

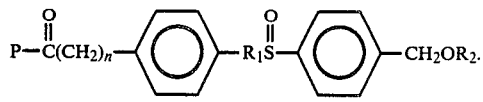

The ester of step (1) can be easily obtained by reacting a (halomethyl)phenylalkylcarboxylic acid with a R-protecting group:

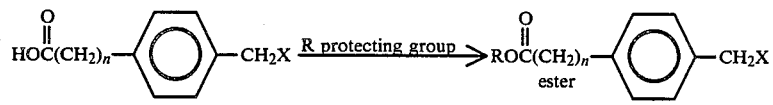

Synthesis I is summarized below:

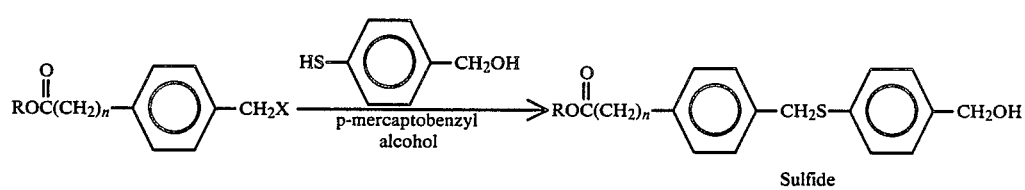

(1)

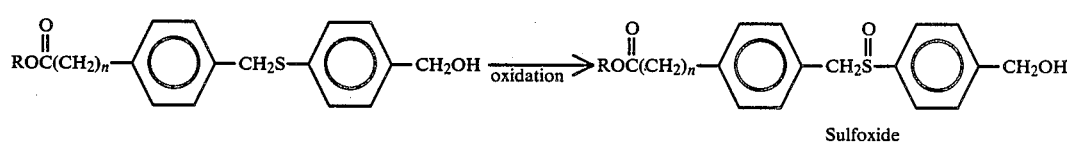

(2)

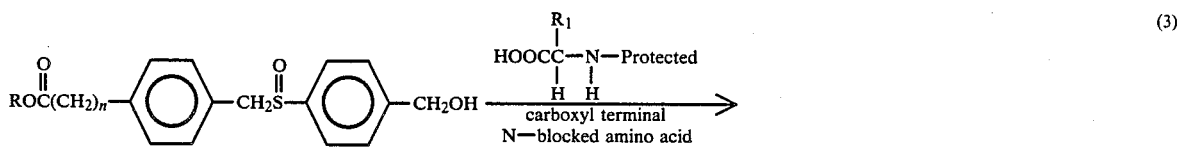

(3)

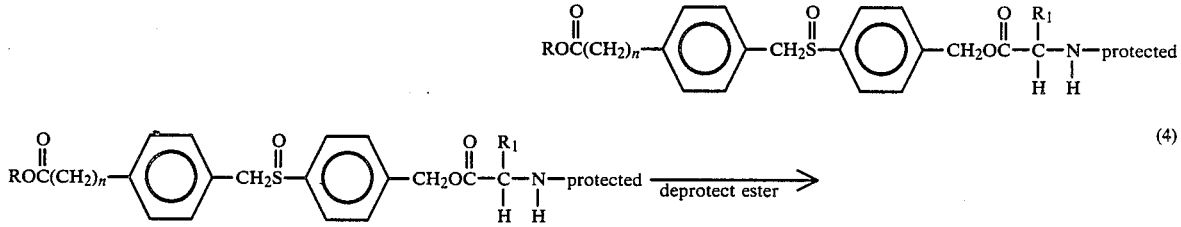

(4)

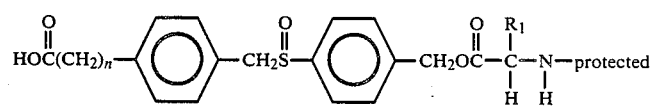

-continued

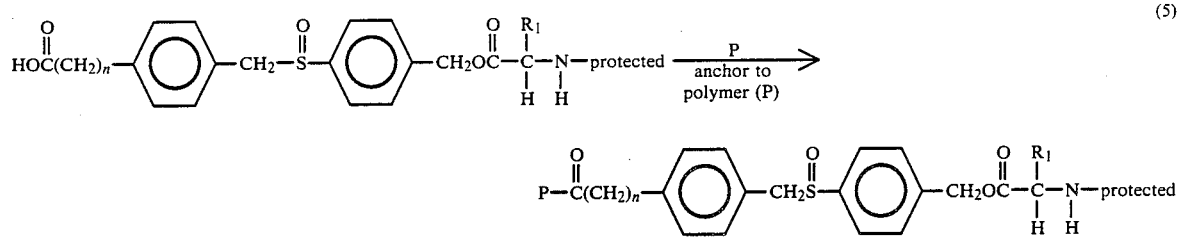

(5)

Synthesis II

A method of synthesizing a resin for solid phase peptide synthesis comprising (1) reacting an ester of the structure

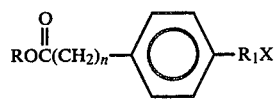

where X is a halogen, n is from 0 to 20, $R_1$ is an alkyl having from 1 to 20 carbons and R is an acid protecting group, with a mercaptobenzyl alcohol to form a sulfide of the structure,

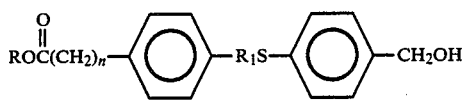

(2) oxidizing the sulfide to form a sulfoxide of the structure,

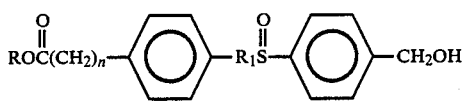

(3) acylating the sulfoxide with an acid, ester, or anhydride, to form an ester, where $R_3$ is an acyl group, of the structure,

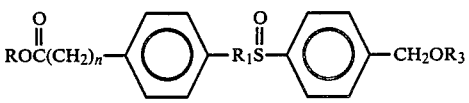

(4) removing the protecting group, R, from the ester to form an acid of the formula

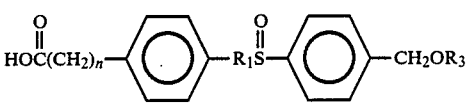

(5) anchoring the sulfoxide to a functionalized polymer, P, to form a resin of the formula

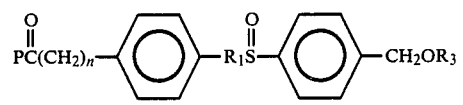

(6) removing the acyl group, $R_3$, to form an alcohol of the formula and

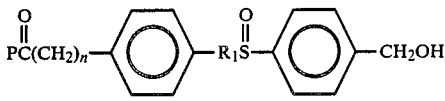

(7) esterifying the alcohol of the sulfoxide with a carboxyl terminal N-blocked amino acid, $R_2$, to form a resin for solid phase peptide synthesis of the formula

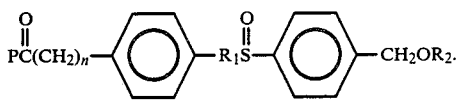

The ester of step (1) can be easily obtained by reacting a (halomethyl)phenylalkylcarboxylic acid with a R-protecting group:

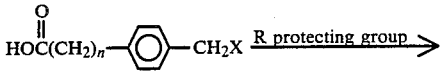

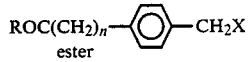

Synthesis II is summarized below:

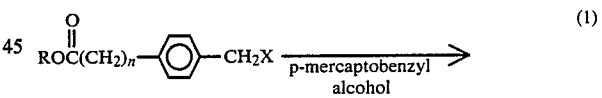

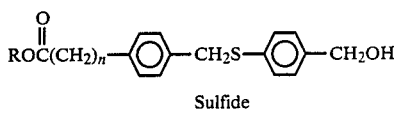

Sulfide

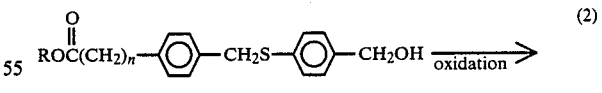

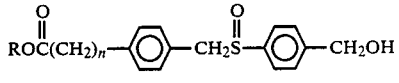

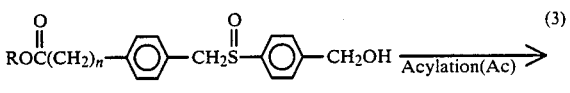

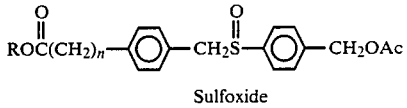

Sulfoxide

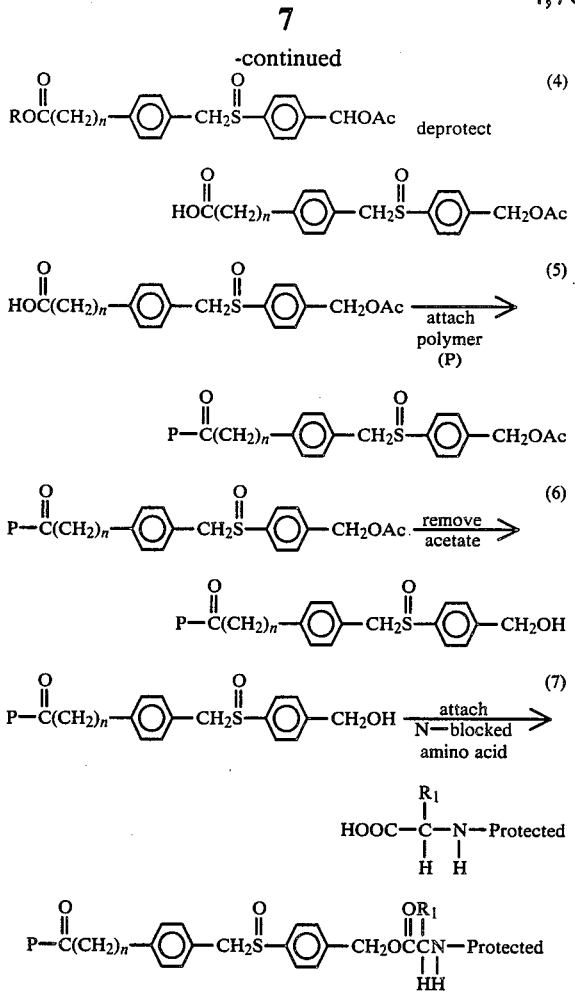

Steps (2) and (3), the oxidation and acrylation respectively, may be reversed.

DETAILED DESCRIPTION OF THE INVENTION

The Resin

The resin of the present invention has the structure

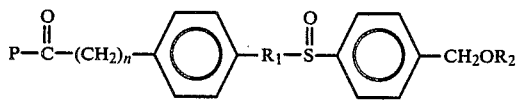

where P is the polymer support, and $R_1$ is an alkyl having from 1 to 20 carbon atoms. A preferred alkyl is methylene. $R_2$ is hydrogen, acyl or a carboxyl terminal N-blocked amino acid, and n is from 0 to 20, preferably 1.

The polymer support can be any of a number of polymers, copolymers or combinations of polymers such as polyamide, polysulfamide, substituted polyethylene, polyethyleneglycol, phenolic resin, polysaccharide, or polystyrene. The polymer support can also be any solid that is insoluble and inert to solvents used in peptide synthesis, such as glass beads. The preferred polymer support is a gel prepared by suspension copolymerization of styrene and about one percent of m-divinylbenzene or crosslinking agent. Such crosslinked gels swell in organic solvents to about 5 to 6 times their dry volume. The swelling allows solvents and reactants access to the reaction sites on the polymer and allows reaction in the interior of the polymer as well as the exterior surface.

Functional groups can be introduced into the polymer by chloromethylation which can be accomplished by using chloromethyl methyl ether. The chloromethylated crosslinked polystyrene gel is referred to in the art as the Merrifield resin. The Merrifield resin is described in further detail in Stewart, J. M. and Young, J. D. *Solid Phase Peptide Synthesis*, second edition, Pierce Chemical Co., Rockford, Ill. which is hereby incorporated by reference. The preferred functional group is amino methyl which can be introduced by the method of Merrifield, *Journal of Organic Chemistry*, vol. 43, no. 14, 1978, pp. 2845–2852.

A preferred resin has the formula

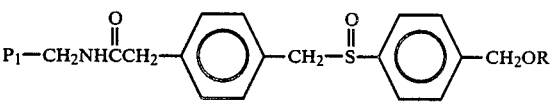

where $P_1$ is a crosslinked polystyrene resin and R is a hydrogen, acyl or carboxyl terminal N-blocked amino acid.

The resin is used for solid phase peptide synthesis. The method of solid phase peptide synthesis is described in detail in copending patent application Serial No. 947,651 which is hereby incorporated by reference. The peptide is synthesized by anchoring an N-protected carboxyl terminal amino acid to the resin, deprotecting the anchored amino acid, neutralizing the amino acid to convert to an amine, coupling a second N-protected amino acid to the amine, repeating the deprotecting and coupling steps to synthesize the desired peptide, reducing the sulfoxide to a sulfide an cleaving the peptide from the resin.

Resin Synthesis I

The ester of Step 1 can be easily obtained by reacting a (halomethyl)phenyl alkylcarboxylic acid of the formula

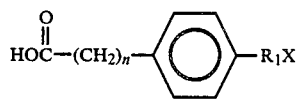

where $R_1$ is an alkyl having from 1 to 20 carbons and n is from 0 to 20, with a protecting group, R, to form an ester. One method of esterifying is to react the (halomethyl)phenyl alkylcarboxylic acid with a halogen source such as thionyl chloride or phosphorous halide to form the acid halide. The acid halide is reacted with any acid protecting group, R, known to those skilled in the art, such as 2-trimethylsilylethanol or 9-fluorenemethanol, in the presence of a base such as pyridine, triethylamine, N,N-dimethyl-4-aminopyridine imidazole or diisopropylethylamine to form an ester. Another method of esterifing is to react the carboxylic acid with a trisubstituted chlorosilane, such as trimethylsilyl chloride, triethylsilyl chloride or t-butyldimethylsilyl chloride, in the presence of a base as described above. Other methods of converting carboxylic acids into esters can be found in T. W. Greene, *Protective Groups in Organic Synthesis*, Wiley and Sons, 1981, pp. 152–185 which is hereby incorporated by reference. The halogen of the halomethyl of the ester is displaced with a mercapto benzyl alcohol such as p-mercapto benzyl alcohol or o-mercapto benzyl alcohol in the presence of a base described above to form a sulfide. The sulfide is oxidized to form a sulfoxide by any of the methods known in the art of oxidation. Oxidizing compounds such as hydrogen peroxide, peracids, iodobenzene dichloride, and sodium periodate can be used. The preferred method of oxidation utilizes m-chloroperbenzoic acid in methylene chloride at from 0 to 25° C. The sulfoxide is reacted with the carboxylic acid group of the carboxyl terminal N-blocked amino acid, such as N-butyloxycarbonyl-L-phenylalanine or N-butyloxycarbonyl-O-benzyl-L-tyrosine by methods described in Stewart et al, supra, which is hereby incorporated by reference. The acid protecting group involving silicon can be removed by hydrolysing with a source of nucleophilic fluoride ion such as tetraalkylammonium fluoride or alkali metal fluoride to form the acid. The acid of the sulfoxide is then anchored to a functionalized polymer such as aminomethyl polystyrene or glass to form the resin.

Resin Synthesis II

The first three steps of resin Synthesis II (e.g. through the oxidation of the sulfide) as well as anchoring the sulfoxide to the functionalized polymer, P, and esterifying the alcohol of the sulfoxide are the same as Synthesis I.

The sulfoxide is acylated with an anhydride such as acetic anhydride or trifluoroacetic anhydride, an acid such as acetic acid, trifluoroacetic acid or benzoic acid or esters such as ethyl acetate or methyl acetate. The preferred acylating agent is acetic anhydride. The acylation is effected in the presence of a solvent that will not react with the sulfoxide, such as methylene chloride, chloroform, benzene or toluene and a base as described above in Resin Synthesis I. The preferred solvent is methylene chloride.

The protecting group, R, is removed as described in Synthesis I. Additionally, R can be removed with a strong acid such as trifluoroacetic acid.

The acyl group is removed by using a nucleophile such as a hydroxide, e.g., sodium hydroxide or potassium hydroxide or hydrazine. The preferred nucleophile is hydrazine. The acyl group is removed in the presence of a solvent that will swell the resin such as N,Ndimethylformamide (DMF), methylene chloride, THF, benzene or toluene. The preferred solvent is DMF.

The following examples are for illustrative purposes only and are not intended to limit the claimed invention in any way.

EXAMPLE 1

Resin Synthesis I

This example illustrates the preparation of a sulfoxide compound, to which a carboxy terminal N-blocked amino acid has been attached (for this example, N-butyloxy-carbonyl (Boc)-L-phenylalanine), and its subsequent attachment to an amino-substituted support (for this example, aminomethylated polystyrene/1% divinylbenzene). This provides a support suitable for solid phase peptide synthesis, with the first amino acid joined to the sulfoxide moiety prior to attachment to the resin:

1. Preparation of β-(trimethylsilyl)ethylpara-(mercapto-4-hydroxymethylphenyl)methylphenyl acetate A suspension of 20.02 g (0.087 moles) of 4-(bromomethyl)phenylacetic acid in 100 ml of chloroform was placed under a nitrogen atmosphere and 12 ml (19.4 g, 0.16 moles) of thionyl chloride was added over five minutes. After the addition of thionyl chloride, 0.5 ml of N,N-dimethylformamide was added all at once and the reaction mixture refluxed for 1.5 hours. After cooling to room temperature, the volatiles were removed under reduced pressure to afford a yellow solid whose $^1$H NMR spectrum indicated a 55:45 mixture of acid chlorides(X=Br and Cl); $^1$H NMR(δ, CDCl$_3$) 7.45- 7.10(m, 4H), 4.55 and 4.42 (singlets, 2H) and 4.11 (s, 2H) identified as p-halomethyl phenylacetyl chloride.

The yellow solid was dissolved in 60 ml of dry tetrahydrofuran under a N$_2$ atmosphere and cooled in the range of 0°-5° C. A solution of 8 ml (7.8 g, 0.10 mol) of pyridine and 13.4 ml (11.6 g, 0.10 mol) of 2-trimethylsilylethanol in 35 ml of dry tetrahydrofuran was added over a fifteen minute period. After stirring at room temperature for one hour, the precipitate of pyridinium hydrochloride was filtered and washed with dry tetrahydrofuran. The combined filtrates were stripped under reduced pressure and dissolved in methylene chloride. After washing twice each with 100 ml of 0.2 N aqueous hydrochloric acid and then water, the organic layer was dried with magnesium sulfate, filtered and stripped under reduced pressure to afford 26.86 g of a yellow oil which when analyzed by gas chromatography on an HP-530 methyl silicone column (10 m×0.53 mm, inj. temp.=280; det. temp.=280; column temp. program=80° C. to 280° C. at 10° C. per min.) proved to be a mixture of esters (X=Br and Cl) with an overall purity of 92% as determined by area percent integration. $^1$H NMR of the crude material (δ, CDCl$_3$) 7.38 (s, 4H), 4.60 and 4.51 (singlets, 2H), 4.36–4.15 (m, 2H), 3.68 (s, 2H), 1.19–0.97 (m, 2H) and 0.08 (s, 9H) identified as β-(trimethylsilyl)ethyl-p-halomethylphenyl acetate.

To a solution of 20.00 g (≈ 0.065 mol) of the above crude product in 100 ml of dry tetrahydrofuran under a nitrogen atmosphere and at 0° C., was added a solution of 10.1 g (0.072 mol) of 4-(mercapto)benzyl alcohol in 30 ml of dry tetrahydrofuran. To the resulting solution was added 15 ml (10.9 g, 0.11 mol) of triethylamine over a fifteen minute period. After removing the ice bath the reaction mixture was stirred at room temperature for one hour, the precipitate filtered and the solvent removed under reduced pressure to afford 26.5 g of a yellow oil. This was chromatographed on silica gel using a Waters Prep 500A chromatograph and eluting with 20% ethyl acetate/hexane to yield 14.1 g (42% overall yield) of a clear colorless oil which crystallized upon standing, mp 41°-42° C.; $^1$H NMR (δ, CDCl$_3$) 7.40–7.10(m, 8H), 4.60(s, 2H), 4.30–4.08(m, 2H), 4.08(s, 2H), 3.57(s, 2H), 2.35(s, 1H), 1.11–0.90(m, 2H) and 0.07(s, 9H); mass spectrum (m/e) 3.88(m+), 360, 345, 287, 249(100%) and 73, identified as β-(trimethylsilyl)ethyl-para-(mercapto-4-hydroxymethylphenyl)-methylphenyl acetate.

2. Preparation of β-(trimethyl-silyl)ethyl-para-(sulfinyl-4-hydroxymethylphenyl)-methylphenyl acetate To a solution of 12.007 g (0.0309 mol) of the purified sulfide from above in 270 ml of methylene chloride at 0°

C., was slowly added 6.3646 g of 83.3% metachloroperbenzoic acid (5.3017, 0.0305 mol) over a twenty minute period. After stirring at ice temperature for 1 hr, the reaction was transferred to a cold room at 7° C. and stirred overnight for twenty hours. To the reaction was added 100 ml of saturated aqueous sodium bicarbonate solution, the layers separated and the organic layer was washed with 100 ml saturated sodium bicarbonate and 100 ml water. After drying over magnesium sulfate and filtering, the solvent was removed under reduced pressure to afford 12.50 g (100%) of a white powder, mp 132°–134° C.; $^1$H NMR ($\delta$, CDCl$_3$) 7.49–7.25(AB quartet, 4H), 7.25–6.90 (AB quartet, 4H), 4.70(s, 2H), 4.31–4.12(m, 2H), 4.00(broad s, 2H), 3.83(broad s, 1H), 3.59(s, 2H), 1.14–0.91(m, 2H) and 0.09(s, 9H); mass spectrum (m/e) 405 (M+H), 377 and 249 (100%) identified as $\beta$-(trimethylsilylethyl)-para-(sulfinyl-4-hydroxymethylphenyl)-methylphenyl acetate.

3. Attachment of first amino acid to sulfoxide compound

To a solution of 2.02 g (4.99 mmol) of the sulfoxide from above, 1.60 g (6.00 mmol) of N-t-butyloxycarbonyl-L-phenylalanine and 61.8 mg (0.51 mmol) of N,N-dimethyl-4-aminopyridine in 75 ml of methylene chloride at room temperature and under a nitrogen atmosphere, was added 7.5 ml of a 1.0 M solution (7.5 mmol) of 1,3-dicyclohexylcarbodiimide. After one hour, 1.0 ml of acetic acid was added and the mixture stirred for another 0.5 hour. The reaction mixture was filtered and washed twice with 100 ml of saturated aqueous sodium bicarbonate solution and then twice with 100 ml of 0.2 N hydrochloric acid solution. After drying with magnesium sulfate and filtering, the methylene chloride was removed under reduced pressure to afford a white solid which was dissolved in 10 ml of ethyl acetate, filtered and cooled to 0° C. After again filtering, the ethyl acetate was removed under reduced pressure to afford 3.26 g (90% yield) of a white solid identified as $^1$H NMR ($\delta$, CDCl$_3$) 7.30–6.88(m, 13H), 5.12(s, 2H), 5.08(d, J=7 Hz, 1H, NH) 4.70–4.40(br m, 1H), 4.30–4.05(m, 2H), 4.00(s, 2H), 3.57(s, 2H), 3.09(d, J=7 Hz, 2H), 1.43(s, 9H), 1.13–0.91(m, 2H), and 0.09(s, 9H); mass spectrum (FAB, m/e) 658(M+Li), 552 and 524 identified as [$\beta$-trimethylsilylethylpara-(sulfinyl-4-hydroxymethylphenyl)-methylphenyl acetate] ester of N-t-butyloxycarbonyl-L-phenylalanine.

4. Removal of $\beta$-trimethylsilyl protecting group ion

To a solution of 3.08 g (4.72 mmol) of the Boc-phenylalanine sulfoxide compound from above, in 15 ml of dry tetrahydrofuran at 0° C. and under a nitrogen atmosphere, was added 13.5 ml of a 1.0 M solution (13.5 mmol) of tetrabutylammonium fluoride in tetrahydrofuran. There was an immediate red color which disappeared after approximately five minutes. The ice bath was removed and the reaction stirred at room temperature for three hours. The tetrahydrofuran was removed under reduced pressure, methylene chloride added and the organic phase washed three times with 0.2 N hydrochloric acid and three times with water. After drying with magnesium sulfate and filtering, the organic phase was removed under reduced pressure to afford 2.51 g (97%) of a white foamy solid. $^1$H NMR ($\delta$, CDCl$_3$) 7.40–6.83(m, 13H), 5.13(s, 2H), 5.08(br s, 1H), 4.63–4.44(br m, 1H), 4.04(br s, 2H), 3.59(s, 2H), 3.00(d, J=7 Hz, 2H) and 1.43(s, 9H); FAB mass spectrum (m/e) 558(M+Li), 552(M+H), 551(M+), 496, 452, 303, 287 and 149 identified as the [para(sulfinyl-4-hydroxymethyl phenyl) methylphenyl acetic acid] ester of N-t-butyloxycarbonyl-L-phenylalanine.

5. Attachment of [para-(sulfinyl-4-hydroxymethyl phenyl) methylphenyl acetic acid] ester of N-t-butyloxycarbonyl-L-phenylalanine to Resin A 0.50 g (0.31 mmol) sample of aminomethylated polystyrene/1% divinylbenzene (Peptides International, 0.62 meq/g) was suspended in 5 ml of methylene chloride, then washed twice with 5 ml of 10% diisopropylethylamine/methylene chloride (v:v) and six times with 5 ml of methylene chloride. To the resin was then successively added 5 ml of 50:50 (v:v) methylene chloride/N,N-dimethylformamide, 151 mg (0.98 mmol) of 1-hydroxybenzotriazole, 249 mg (0.45 mmol) of the Boc-L-Phe sulfoxide handle and then 0.20 ml (160 mg, 1.27 mmol) of 1,3-diisopropylcarbodiimide. After shaking for 2.5 hours, the solvent was removed and the resin washed three times with 5 ml of methylene chloride and three times with 5 ml of methanol. After drying under vacuum for fifteen hours, the resin weighed 660 mg and showed a phenylalanine loading of 0.459 meq/g when submitted for amino acid analysis. Infrared analysis of this resin showed a medium intensity band at 1030 cm$^{-1}$, indicative of the sulfoxide group, and a strong band at 1670 cm$^{-1}$, indicative of the amide bond to the resin. Other strong bands were found at 1740, 1720, 1520 and 1170 cm$^{-1}$, which were assigned to the N-Boc-L-phenylalanine group.

EXAMPLE 2

Resin Synthesis II

The following example illustrates the preparation of a sulfoxide compound and its attachment to an amino-substituted support (for this example, aminomethylated polystyrene/1% divinylbenzene). This provides a support suitable for solid phase peptide synthesis which contains a para-sulfinyl-benzyl alcohol group, to which the C-terminal amino acid of the desired peptide can be attached.

Steps 1 and 2 are the same as described in Example 1 above.

3. Preparation of $\beta$-(trimethyl-silyl)ethyl-para-(sulfinyl 4-acetoxymethylphenyl)methylphenyl acetate To 3.00 g (7.41 mmol) of the alcohol from Step 2 of Example 1 and 0.09 g (0.74 mmol) of N,N-dimethyl-4-aminopyridine in 25 ml of methylene chloride at room temperature and under a nitrogen atmosphere, was added 0.75 ml (0.84 g, 8.22 mmol) of acetic anhydride. After stirring for one hour, the methylene chloride solution was washed successively with 0.2 N hydrochloric acid and saturated aqueous sodium bicarbonate, dried with magnesium sulfate, filtered and the solvent removed under reduced pressure to afford 3.21 g (97%) of a white solid, mp 136°–137° C. $^1$H NMR ($\delta$, CDCl$_3$) 7.41(s, 4H), 7.22–6.96(AB quartet, 4H), 5.14(s, 2H), 4.23–4.15(m, 2H), 4.09–3.96(AB quartet, 2H), 3.58(s, 2H), 2.13(s, 3H), 1.02–0.94(m, 2H) and 0.05(s, 9H); FAB mass spectrum (m/e) 469(M+Na), 447(M+H) and 419 indicating th desired compound.

4. Preparation of para-(sulfinyl-4'-acetoxymethylphenyl)methylphenylacetic acid To 2.54 g (5.69 mmol) of the product of Step 3, was added 50 ml of 45% trifluoroacetic acid/5% anisole/50% methylene chloride (v:v:v). After forty-five minutes at room temperature, the volatiles were removed under reduced pressure to afford 1.98 g of a white solid, mp 165°–166° C.; $^1$H NMR ($\delta$, CDCl$_3$ and d$_6$-DMSO) 7.55 (s, 4H), 7.31 (d, J=7.3 Hz, 2H), 7.11 (d, J=7.3 Hz, 2H), 5.25 (s, 2H), 4.03 (s, 2H), 3.57 (s, 2H) and 2.14 (s, 3H); mass spectrum (m/e) 347 (M+1), 303 and 149 indicating the desired compound.

5. Attachment of para-(sulfinyl-4'-acetoxymethylphenyl)methyl phenylacetic acid to an aminomethylated polystyrene resin A 2.00 g (1.18 mmol) sample of aminomethylated polystyrene/1% divinylbenzene (Peptides International, 0.59 meq/g) was placed in a shaker vessel and washed twice with 20 ml of 10% (v:v) diisopropylethylamine/methylene chloride, six times with 20 ml of methylene chloride and then twice with 50% N,N-dimethylformamide/50% methylene chloride (v:v). To the resulting wet resin, was sequentially added 20 ml of 50% N,N-dimethylformamide/50% methylene chloride (v:v), 0.66 g (1.90 mmol) of the acid obtained from Step 4, 0.58 g (3.78 mmol) of 1-hydroxybenzotriazole and 2.0 ml (1.6 g, 12.7 mmol) of 1,3-diisopropylcarbodiimide. After shaking for twenty-four hours, the solution was drained and the resin was washed six times with 25 ml of methylene chloride. A sample of resin was removed and dried under vacuum. Infrared analysis of this sample showed strong bands at 1740 cm$^{-1}$ (ester carbonyl), 1675 cm$^{-1}$ (amide carbonyl) and 1030 cm$^{-1}$ (sulfoxide) indicating the desired compound.

6. Removal of acetate group

The resin obtained from Step 5 was washed three times with 25 ml of N,N-dimethylformamide and then a solution of 3 ml (3.0 g, 95 mmol) of anhydrous hydrazine in 25 ml of N,N-dimethylformamide was added. After shaking for forty-eight hours, the solution was drained and the resin washed successively three times each with 25 ml of N,N-dimethylformamide, methylene chloride and isopropanol. After drying under vacuum a sample was characterized by its infrared spectrum and showed strong bands at 1660 cm$^{-1}$ (amide carbonyl) and 1030 cm$^{-1}$ (sulfoxide). The ester band at 1740 cm$^{-1}$ found in the infrared spectrum of the resin from Step 5 was no longer present.

EXAMPLE 3

The following example illustrates the attachment of an N-protected amino acid (for this example, Boc-L-phenylalanine) to the sulfoxide handle substituted resin of Example 2.

The resin from Step 6 of Example 2 (approx. 1.18 mmol) was washed three times with 20 ml of methylene chloride and then 20 ml of methylene chloride, 0.78 g (2.94 mmol) of N-butyloxycarbonyl-L-phenylalanine, 0.02 g (0.16 mmol) of N,N-dimethyl-4-aminopyridine and 1.0 ml (0.80 g, 6.35 mmol) of 1,3-diisopropylcarbodiimide were sequentially added. After shaking for twenty-four hours, the solution was drained and the resin washed three times with 20 ml of methylene chloride. After suspending in 20 ml of methylene chloride, 1.6 ml (1.2 g, 9.2 mmol) of diisopropylethylamine and 1.0 ml (1.1 g, 11 mmol) of acetic anhydride were added. After shaking for two hours the solution was drained, the resin washed three times with methylene chloride and three times with methanol, and then dried under vacuum. Amino acid analysis of this resin showed a phenylalanine loading of 0.46 meq/g. Infrared analysis of this resin showed showed a medium intensity band at 1030 cm$^{-1}$ indicative of the sulfoxide group, and a strong band at 1670 cm$^{-1}$, indicative of the amide band to the resin. Other strong bands were found at 1740, 1720, 1520 and 1170 cm$^{-1}$, which were assigned to the N-Boc-L-phenylalanine group. The infrared spectrum of this resin was identical to that of the resin from Step 5 of Example 1.

I claim:

1. A resin for solid phase peptide synthesis comprising the structure

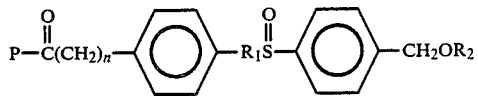

where R$_1$ is an alkyl having from 1 to 20 carbons, R$_2$ is hydrogen, acyl or carboxyl terminal N-blocked amino acid, n is from 0 to 20 and P is a polymer support.

2. The resin of claim 1 wherein P is a functionalized crosslinked polystyrene.

3. The resin of claim 2 wherein R$_1$ is methylene, R$_2$ is a carboxyl terminal N-blocked amino acid and n is 1.

4. A resin for solid phase peptide synthesis comprising the structure

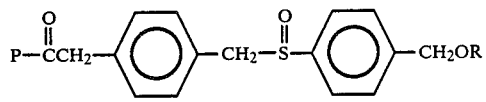

where P is a crosslinked polystyrene and R is hydrogen, a carboxyl terminal N-blocked amino acid or an acyl group.

* * * * *